(12) United States Patent
Park et al.

(10) Patent No.: US 7,851,198 B2
(45) Date of Patent: Dec. 14, 2010

(54) L-LYSINE-INDUCIBLE PROMOTER

(75) Inventors: Young Hoon Park, Seongnam-si (KR); Hyun Min Koo, Yongin-si (KR); Jun Ok Moon, Seoul (KR); Seong Jun Kim, Suwon-si (KR); Hyo Jin Kim, Daejeon (KR); Jung Kee Lee, Daejeon (KR)

(73) Assignee: CJ Cheiljedang Corporation, Seoul (KR)

( * ) Notice: Subject to any disclaimer, the term of this patent is extended or adjusted under 35 U.S.C. 154(b) by 745 days.

(21) Appl. No.: 11/794,688

(22) PCT Filed: Dec. 30, 2005

(86) PCT No.: PCT/KR2005/004675

§ 371 (c)(1),
(2), (4) Date: Jul. 2, 2007

(87) PCT Pub. No.: WO2006/071099

PCT Pub. Date: Jul. 6, 2006

(65) Prior Publication Data

US 2010/0047900 A1 Feb. 25, 2010

(30) Foreign Application Priority Data

Dec. 30, 2004 (KR) ...................... 10-2004-0117104

(51) Int. Cl.
C12N 1/20 (2006.01)
C07H 21/02 (2006.01)
C07H 21/04 (2006.01)
(52) U.S. Cl. .................................. 435/252.32; 536/23.1
(58) Field of Classification Search ........................ None
See application file for complete search history.

(56) References Cited

U.S. PATENT DOCUMENTS

2002/0197605 A1* 12/2002 Nakagawa et al. ............. 435/6

FOREIGN PATENT DOCUMENTS

| EP | 1790721 A1 | 5/2007 |
|---|---|---|
| KR | 1020010049729 A | 6/2001 |
| KR | 1020020097245 A | 12/2002 |
| KR | 1020030040712 A | 5/2003 |
| WO | WO 02/40679 | 5/2002 |
| WO | WO/2005/056800 | * 6/2005 |

OTHER PUBLICATIONS

Pubmed Genbank Accession No. BX927153, "*Corynbacterium glutamicum* ATCC 13032, is Fingerprint Type 4-5, Complete Genome" (Jan. 26, 2004).
Pubmed Genbank Accession No. BX927154, "*Corynbacterium glutamicum* ATCC 13032, is Fingerprint Type 4-5, Complete Genome; Segment 7/10" (Jan. 26, 2004).
Pubmed Genbank Accession No. BX927156, "*Corynbacterium glutamicum* ATCC 13032, is Fingerprint Type 4-5, Complete Genome; Segment 9/10" (Jan. 26, 2004).
Pubmed Genbank Accession No. BX927157, "*Corynbacterium glutamicum* ATCC 13032, is Fingerprint Type 4-5, Complete Genome; Segment 10/10" (Jan. 26, 2004).
Patek, M. et al "Promoters of *Corynebacterium glutamicum*" Journal of Biotechnology, vol. 104(1-3), pp. 311-323 (Sep. 4, 2003).
Schmitt, M. P. et al "Transcription of the *Corynebacterium diphtheriae* HMUO Gene is Regulated by Iron and Heme" Infection and Immunity, vol. 65(11) pp. 4634-4641 (Nov. 1997).
Vasicova, P. et al, "Analysis of the *Corynebacterium glutamicum* Dapa Promoter" Journal of Bacteriology, 181, 6188-6191 (Oct. 1999).
Eikmanns, B.J. et al, "A Family of *Cornebacterium glutamicum/ Escherichia coli* Shuttle Vectors for Cloning, Controlled Gene Expression, and Promoter Probing," Gene 102, 93-98 (1991).
Patek, M. et al, "Promoters From *Corynebacterium glutamicum*: Cloning, Molecular Analysis and Search for a Consensus Motif" Microbiology, 142, 1297-1309 (1996).
English Translation of Abstract: Korean Publication No. KR 1020010049729(A); Applicant: DEGUSSA AG; Published: Jun. 15, 2001 (Abstract Only) (1 PG).
English Translation of Abstract: Korean Publication No. KR 1020020097245(A); Applicant: DEGUSSA GMBH; Published: Dec. 31, 2002 (Abstract Only) (1 PG).
English Translation of Abstract: Korean Publication No. KR 1020030040712(A); Applicant: Applicant CJ Corp; Published: May 23, 2003 (Abstract Only) (1 PG).
PUBMED GENBANK Accession No. BX927153, "*Corynbacterium glutamicum* ATCC 13032, is Fingerprint Type 4-5, Complete Geneome" (Jan. 26, 2004).
PUBMED GENBANK Accession No. BX927154, "*Corynbacterium glutamicum* ATCC 13032, is Fingerprint Type 4-5, Complete Geneome; Segment 7/10" (Jan. 26, 2004).
PUBMED GENBANK Accession No. BX927156, "*Corynbacterium glutamicum* ATCC 13032, is Fingerprint Type 4-5, Complete Geneome; Segment 9/10" (Jan. 26, 2004).
PUBMED GENBANK Accession No. BX927157, "*Corynbacterium glutamicum* ATCC 13032, is Fingerprint Type 4-5, Complete Geneome; Segment 10/10" (Jan. 26, 2004).

* cited by examiner

*Primary Examiner*—Robert A. Zeman
*Assistant Examiner*—Nina A Archie
(74) *Attorney, Agent, or Firm*—Casimir Jones, S.C.

(57) ABSTRACT

Disclosed is a novel L-lysine-inducible promoter nucleic acid molecule. Also disclosed are a vector containing the nucleic acid molecule, a host cell transformed with the vector, and a method of inducing expression of a target gene using the L-lysine-inducible promoter nucleic acid molecule.

2 Claims, 2 Drawing Sheets

Lys (mM)  0    250    500 a b c d e

SEQUENCE LISTING

<160> NUMBER OF SEQ ID NOS: 15

<210> SEQ ID NO 1
<211> LENGTH: 578
<212> TYPE: DNA
<213> ORGANISM: C.glutamicum

<400> SEQUENCE: 1

```
aaccccgtag caaccagcga ctcactgacc acggtggctg ctgaggcctt gagcggcacg      60
atttcatcgc gctcgggcag atatttggtg gcaccttcgt ggcgcgcggc ggtgtacagc     120
accccggtga ccacattgat cacagcacct gccacgacct cgccgtcgat cgccgcagcg     180
atcgagacgg cgtattgggg caggtcataa aggaagttga cggtgccgtc aatggggtcg     240
acgatccagg taactccgct tatcgacgcc gtccccgtcc cttcctcgcc tatcagcccg     300
tctttaggcc gaagttcctg caacctattg gcgataaaat cttcagccaa agtatctact     360
atcgtcaccg gatcgactgt cgaacttttg gtgttggtgt agtcccacaa attggtgagt     420
tcagcacgct tatccctgat acgtacagcg gtaagcgtgg cagtttccgc ggcgatggca     480
cgcaactcat taaacgattg ttgttccata agaccatcat cgttgttttt ttagaaaatt     540
gcctgccaaa agccgaagta atttgtacac ttgggcgc                             578
```

<210> SEQ ID NO 2
<211> LENGTH: 500
<212> TYPE: DNA
<213> ORGANISM: C.glutamicum

<400> SEQUENCE: 2

```
ttgcctctag tgggactggc tatgaaccga acgcagtgcc ggactacatc cgatgatttt      60
ctcattgatc ccctgcatat cactgacggt gatgtaggcg aggaaatcga agcatatcta     120
gtgggtgcct actgcatcga agatgagctg attttacgcc ggcgaatccg cttcccgaga     180
ggagtcaaac caggagatat catcggaatt cctaacaccg caggatactt catgcatatc     240
ttggaaagtg catcgcacca aatcccgttg gcgaaaaatg tagtgtggcc ggaggggcag     300
ttagacgata tcgatgcgga ttaagacata accattcgct aatctttcga cgccccttct     360
gaggtgggga tttcttttca tcccctttaa ttattttcgg aaatttatac agcaatcctc     420
gaaatcctaa taaagatccc ttatcgtggg agaggtacgg tagttcgttc gaggacaacg     480
```
tcgagaaagg catgatttca                                                500

<210> SEQ ID NO 3
<211> LENGTH: 498
<212> TYPE: DNA
<213> ORGANISM: C.glutamicum

<400> SEQUENCE: 3
atttcagcct gaaccttctc attgatgaca cttcaggctt gtgcctcctg cactaatga     60
ggggaggttg tgatttctta catagtttag cgttcgtccg ccttgcgtac agcccggttt    120
gcaaagtttt attttgtaat tttcaaaccg atctcaattc cacgctttga gcagcacaaa   180
tgcttattgc cgtagaaaac aatacggagc ggttacaagt tgcgaagcac cctttgcaaa   240
gttttttagcg gtactttaca gctcttcacc ccccattaat ggggtctatg aaagcgcgca  300
gcgtgacaaa tctgacccca gcaaagcccc caatactccc cgactggcct ttattagtct   360
gcacttacca cgtatcatgg agggttgata gcagggcacc attagcagtc gcaccccgat   420
aggagtcgaa tctacaagtg gaacccccgc tcacatactc cacattttt agaacccctt    480
taaggaatcg aactttat                                                498

<210> SEQ ID NO 4
<211> LENGTH: 498
<212> TYPE: DNA
<213> ORGANISM: C.glutamicum

<400> SEQUENCE: 4
tgcttaattt cctcggcatg gttaagcggc tcggtgccgt cgattttcca ttggccttcg     60
ggcttaggct tcctggcggc acgtgctggc cgggcacttc cggtggttgt tgtcatgggg   120
agttaatcct taaagagcta gtgaagtaca tgtcactcgg tttgatctat ccgcaaactt   180
agacgtaccg ctctgtctag accaaccatt agattcatga gactgaaagc aatggagtca   240
cctaatgccc gtttaaatga attaacctgg ggatattagg ttaggttcac cgtgaatata   300
atagaccgat ctgtctagtt тттттcaтgga gттттgaaттт aattaagcaa aagtcttcgc   360
attgtcgcat tcgctgcta cgtttacaga ccaagcggtc taggagtgtt aaacagcctg   420
gacttgaaac accттттaacт acттgaттттт cacaccccттg tttccataaa agggctcacg  480
aaaggcaact tcaaacac                                                498

<210> SEQ ID NO 5
<211> LENGTH: 498
<212> TYPE: DNA
<213> ORGANISM: C.glutamicum

<400> SEQUENCE: 5
atggctgcgc atactgttgc gatggttgac gcgaagcgca gtcgcgaaac cccgcaggcg     60
cctgtttccg ctgaaattga agaggccggt ggtgtgacta ttacctcgcc gattatcaac   120
aagactccgc tgaatgcccc caagattgac ttggatgcag tgcgtagagc tgcggaaact   180
acgcaagaac ccaaaaatga ttaataattg agacaagctt cccactatgt gataaagtcc   240
catттттgтga ataactcttg tctcagtcaa agcacccagt ggtggtggcg cgctaactaa   300
gcgagcctga cacctcaagt tgttttcact ttgatgaatt тттттaaggcт cgtacttcgt    360
tcgacgaaga agcgggcctt ttgttggttt ттagcccacaa ccggcaagcc ctggatcgaa   420
tgaagctcgc agcgagtaat tatttgatgt tcccagaaa ggcttcagcc ccacaatgat      480

```
ttcctcggta ggtgcccc                                                        498
```

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6

```
ttggatccaa ccccgtagca accagc                                                26
```

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7

```
gaggatccgc gcccaagtgt acaaatt                                               27
```

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8

```
atggatcctt gcctctagtg ggactg                                                26
```

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9

```
taggatcctg aaatcatgcc tttctcg                                               27
```

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10

```
taggatccat ttcagcctga accttc                                                26
```

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11

```
caggatccat aaagttcgat tccttaaa                                              28
```

<210> SEQ ID NO 12
<211> LENGTH: 26
<212> TYPE: DNA
<213> ORGANISM: Artificial Sequence

```
<220> FEATURE:
<223> OTHER INFORMATION: Synthetic

<400> SEQUENCE: 12
acggatcctg cttaatttcc tcggca                                          26

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
atggatccgt gtttgaagtt gcctttt                                         26

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
aaggatccat ggctgcgcat actgttg                                         27

<210> SEQ ID NO 15
<211> LENGTH: 26
<212> TYPE: DNA
<213> ORGANISM: Artificial Sequence
<220> FEATURE:
<223> OTHER INFORMATION: Synthetic

<400> SEQUENCE: 15
atggatccgg ggcacctacc gaggaa                                          26
```

L-LYSINE-INDUCIBLE PROMOTER

TECHNICAL FIELD

The present invention relates to a novel L-lysine-inducible promoter nucleic acid molecule, a vector containing such a nucleic acid molecule, a host cell transformed with the vector, and a method of inducing expression of a target gene using the L-lysine-inducible promoter nucleic acid molecule.

BACKGROUND ART

Coryneform bacteria are industrial microorganisms that produce chemical substances having various applications in the industry of animal feed, drugs, food, and the like, which contain L-lysine, L-threonine and various nucleic acids. To develop high titer strains from such coryneform bacteria by genetic engineering or metabolic engineering, the expression of genes involving several metabolic pathways in coryneform bacteria should be selectively regulated. Thus, promoter sequences useful for this gene regulation are required.

Upon the gene expression in coryneform bacteria, genes are generally expressed from their own promoters (Vasicova, P., et al., J. Bacteriol. 181, 6188-6191, (1999), etc.). However, unlike other industrial microorganisms such as *Escherichia coli* and *Bacillus subtilis*, there is no information on the basic structure of promoter sequences for gene expression in coryneform bacteria. For this reason, promoters have been developed by eliminating promoter regions from genes associated with resistance to antibiotics such as chloramphenicol, introducing chromosomal DNA isolated from coryneform bacteria and digested with suitable restriction enzymes into the promoter sites, transforming coryneform bacteria with the resulting DNA molecules, assessing antibiotic resistance of obtained strains (Eikmanns, B. J., et al., Gene, 102, 93-98, (1991); Patek, M., et al., Microbiology, 142, 1297-1309, (1996)). However, previously developed promoter sequences still need to be improved with respect to selective expression and expression efficiency of genes of interest.

Conventional methods involving promoter isolation include (1) the use of a promoter probe vector system in the random cloning of genomic DNA fragments upstream of a reporter gene expressed only when a cloned fragment contains promoter activity; (2) gene-specific probe-based hybridization by which a gene and its promoter are isolated from a genomic library; and (3) differential hybridization of an inducible cDNA probe and a non-inducible cDNA probe to a gene bank.

Recently developed comparative proteome analysis by two-dimensional (2-D) gel electrophoresis is a technology that identifies proteins differentially expressed at different physiological states. Based on differentially expressed proteins, many studies have been performed to identify regulatory genes capable of increasing expression of the proteins.

Based on this background, the present inventors conducted 2-D gel electrophoresis of proteins whose expression was induced in the presence of lysine, and detected and identified proteins displaying differential expression patterns by comparative analysis of proteomes. When polynucleotides corresponding to the putative promoter regions of the identified proteins were amplified by PCR and were introduced upstream of a promoter-deficient lacZ gene, a remarkable increase in beta-galactosidase activity was observed in the presence of lysine, thereby leading to the present invention, which provides novel promoter nucleic acid molecules capable of inducing gene expression in the presence of lysine.

DISCLOSURE OF THE INVENTION

It is therefore an object of the present invention to provide a novel L-lysine-inducible promoter nucleic acid molecule.

It is another object of the present invention to provide a vector comprising the novel promoter nucleic acid molecule.

It is a further object of the present invention to provide a host cell transformed with the vector.

It is yet another object of the present invention to provide a method of inducing expression of a target gene using the novel promoter nucleic acid molecule.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
FIG. 1 shows the results of 2-D gel electrophoresis of whole-cell lysates of *C. glutamicum* cultured in either the absence or presence of lysine, wherein differentially expressed proteins are indicated by arrows.
Figure 1:
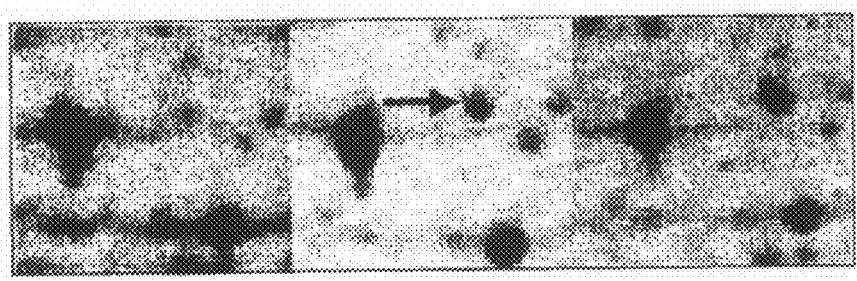
Figure 1:
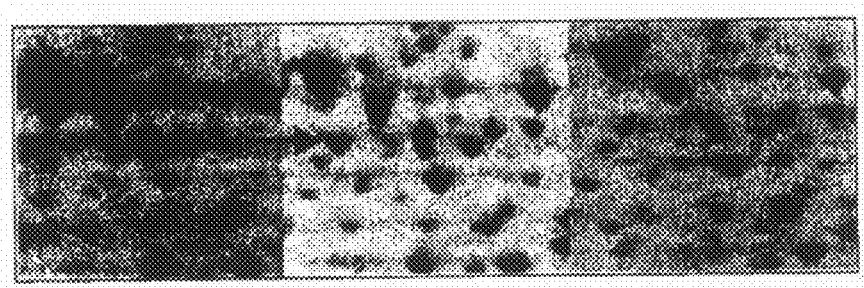
Figure 1:
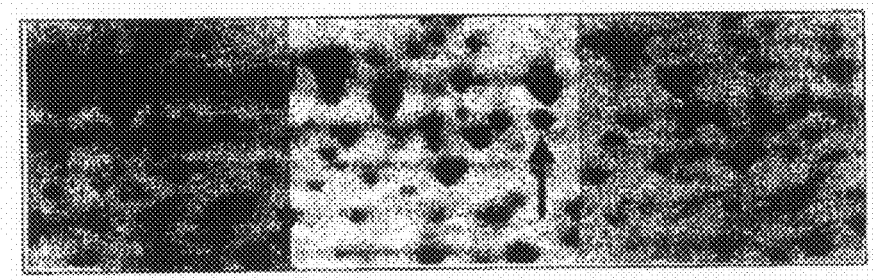
Figure 1:
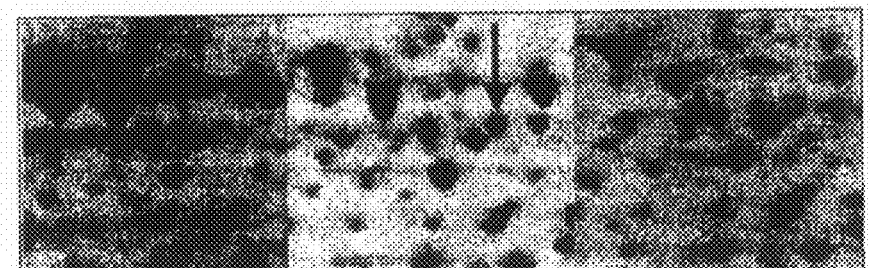

In one aspect, the present invention relates to a novel L-lysine-inducible promoter nucleic acid molecule.

In detail, the L-lysine-inducible promoter nucleic acid molecule of the present invention has the nucleotide sequence of SEQ ID No. 1, 2, 3, 4 or 5.

The nucleotide sequence of the promoter nucleic acid molecule according to the present invention may be modified to a certain degree by any one of several recently developed methods, for example, directed evolution or site-directed mutagenesis. Those skilled in the art readily appreciate that a nucleotide sequence having 70% or higher homology by such artificial modification is derived from and is an equivalent to the nucleotide sequence of the present invention, as long as it retains promoter activity for expressing a target gene.

Thus, the L-lysine-inducible promoter nucleic acid molecule of the present invention includes nucleotide sequences that have 70% or higher homology to the aforementioned nucleotide sequence and are available as L-lysine-inducible promoters.

The term "homology", as used herein, is intended to indicate sequence similarity to the native nucleic acid sequence. The "homology" includes a DNA sequence preferably 75% or higher, more preferably 85% or higher, even more preferably 90% or higher, and most preferably 95% or higher, identical to the nucleotide sequence of the L-lysine-inducible promoter nucleic acid molecule of the present invention. The homology evaluation may be done with the naked eye or using commercially available software. Using a commercially available computer program, the homology between two or more sequences may be expressed as a percentage (%), and the homology (%) between adjacent sequences may be evaluated.

In addition, the L-lysine-inducible promoter nucleic acid molecule of the present invention includes an L-lysine-inducible promoter nucleic acid molecule selected from the group consisting of nucleotide sequences complementary to the aforementioned nucleotide sequence.

The term "complementary", as used herein, refers to the hybridization or base-pairing between nucleotides or nucleic acids, such as, for example, between the two strands of a double-stranded DNA molecule or between an oligonucleotide primer and a primer binding site on a single-stranded nucleic acid to be sequenced or amplified.

The L-lysine-inducible promoter nucleic acid molecule of the present invention also includes a functional equivalent that exerts activity identical to the L-lysine-inducible promoter nucleic acid molecule. The functional equivalent, which includes a functional fragment, may include variants in which one or more nucleotide bases are altered by substitutions, deletions, insertions or combinations thereof.

The L-lysine-inducible promoter nucleic acid molecule of the present invention is derived from coryneform bacteria, and is useful as a promoter for gene expression in prokaryotic cells, particularly *E. coli* and coryneform bacteria.

The term "promoter", as used herein, refers to a DNA region to which RNA polymerase binds to initiate gene transcription, and positions at the 5' direction of an mRNA transcription initiation site. With respect to the objects of the present invention, the promoter of the present invention indicates an L-lysine-inducible promoter that is sufficient to direct promoter-dependent gene expression in the presence of an external signal, L-lysine.

The L-lysine-inducible promoter nucleic acid molecule of the present invention may be isolated or prepared using a standard molecular biology technique. For example, it may be isolated by PCR using proper primer sequences. Also, it may be prepared by a standard synthesis technique using an automated DNA synthesizer.

The term "coryneform bacteria", as used herein, includes microorganisms belonging to the genus *Corynebacterium* or *Brevibacterium*. Such coryneform bacteria include *Corynebacterium glutamicum* ATCC 13032; other wild-type strains known as suitable strains of the genus *Corynebacterium*, particularly the species *Corynebacterium glutamicum*, *Corynebacterium thermoaminogenes* FERM BP-1539, *Brevibacterium flavum* ATCC 14067, and *Brevibacterium lactofermentum* ATCC 13869; and L-amino acid-producing mutants or strains prepared therefrom, for example *Corynebacterium glutamicum* KFCC 10881 and *Corynebacterium glutamicum* KFCC 11001.

In another aspect, the present invention relates to a vector comprising the novel L-lysine-inducible promoter nucleic acid molecule.

The term "vector", as used herein, refers to a DNA construct that contains a DNA sequence which is operably linked to a suitable control sequence. Such control sequences may include a promoter to direct transcription, a certain operator sequence to control such transcription, a sequence encoding a suitable ribosome-binding site on the mRNA, and a sequence to control termination of transcription and translation. The vector may be a plasmid, a phage particle, or simply a potential genome insert. Once transformed into a suitable host, the vector may replicate and function independently of the host genome, or may, in some cases, integrate into the genome itself.

The term "operably linked", as used herein, means that a gene to be expressed is linked to its control sequences in a manner as to be expressed.

After performing 2-D gel electrophoresis, the present inventors identified proteins displayed increased expression by comparative analysis of proteomes, and employed a reporter gene to search promoter sequences from such proteins. A reporter gene is a gene that allows the activity of a promoter of interest to be readily detected through its expression. Available reporter genes include beta-galactosidase, beta-glucuronidase, luciferase, chloramphenicol transacetylase, and fluorescent proteins (e.g., green fluorescent protein, red fluorescent protein, yellow fluorescent protein, blue fluorescent protein, cyan fluorescent protein, etc.).

In a detailed practice of the present invention, to determine whether the novel promoter nucleic acid molecule of the present invention is L-lysine-inducible by measuring the activity of beta-galactosidase, expressed from a lacZ gene, a recombinant vector, pLCP, was constructed. In another detailed practice of the present invention, the pLCP vector containing the L-lysine-inducible promoter nucleic acid molecule of the present invention displayed two or more times higher beta-galactosidase activity in the presence of 250 mM of L-lysine than in the absence of L-lysine.

The present vector containing the L-lysine-inducible promoter nucleic acid molecule is operably linked to any one of genes encoding various proteins in order to recombinantly produce target genes. The target genes to be readily expressed using the present vector include, but are not limited to, asd, dapA, dapc, dapF, fbp, lysC and pyc. Of the target genes, asd, dapA, lysC and pyc are particularly preferred.

In a further aspect, the present invention relates to host cells transformed with the vector.

The aforementioned vector containing the L-lysine-inducible promoter nucleic acid molecule is operably linked to a gene encoding a target protein to induce expression of the target protein. The vector constructed in such a way is transformed into host cells, for example, prokaryotic cells, preferably *E. coli* and coryneform bacteria, and more preferably coryneform bacteria.

The term "transformation", as used herein, means the introduction of DNA into a host in such a way that it can replicate either as an extrachromosomal element or by chromosomal integration.

The cultivation of the thus transformed host cells (transformants) may be performed according to ordinary methods in the art. The known cultivation methods are described by Chmiel (Bioprozesstechnik 1. Einfuhrung in die Bioverfahrenstechnik (Gustav Fischer Verlag, Stuttgart, 1991)); and Storhas (Bioreaktoren und periphere Einrichtungen (Vieweg Verlag, Braunschweig/Wiesbaden, 1994)).

In yet another aspect, the present invention relates to a method of inducing expression of a target gene, which is based on using the L-lysine-inducible promoter nucleic acid molecule.

The novel L-lysine-inducible promoter nucleic acid molecule of the present invention is able to induce high-level expression of a target gene operably linked thereto, and is thus useful in the mass production of a target protein.

A better understanding of the present invention may be obtained through the following examples which are set forth to illustrate, but are not to be construed as the limit of the present invention.

Example 1

Screening and Identification of Proteins Whose Expression is Induced by L-Lysine in *Corynebacterium glutamicum*

(1) Preparation of Protein Samples from *Corynebacterium glutamicum* ATCC 13032 Cultured at Various Concentrations of L-Lysine

*Corynebacterium glutamicum* ATCC 13032 was cultured in the absence or presence of L-lysine (0, 250 and 500 nM), and cells were harvested by centrifugation. The cells were washed three times with 10 mM Tris-HCl buffer (pH 7.5).

The washed cells were resuspended in lysis buffer (7 M urea, 2 M thiourea, 4% CHAPS (3-[(3-chloamidopropyl) dimethyl-ammonio]-1-propanesulfonate), 0.4% dithiothreitol), were disrupted by sonication on ice using a sonicator, and were centrifuged at 12,000×g for 15 min at 4° C. The thus obtained cell lysate was mixed with endonuclease (Sigma) at a final concentration of 700 units/ml and 1× protease inhibitor cocktail (Roche). Protein concentrations were determined by the Bradford method.

(2) Protein Separation by 2-D Gel Electrophoresis

500 µg of each of the obtained protein samples was mixed with solubilization buffer (7 M urea, 2 M thiourea, 4% CHAPS (3-[(3-chloamidopropyl)dimethyl-ammonio]-1-propanesulfonate), 0.4% dithiothreitol, 1% bromophenol blue) to give a final volume of 500 µl, and was centrifuged at 20,000×g for 15 min at 4° C. The supernatant was mixed with 0.5% immobiline pH gradient (IPG) buffer (pH 4.5-5.5 carrier ampolyte, Amersham Pharmacia Biotech). The resulting solution was loaded onto an IPG dry strip rehydration tray, and an 18-cm IPG dry strip with a linear gradient of pH 4.5-5.5 was rehydrated with the protein sample on the rehydration tray for 12 hrs.

The rehydrated strip was subjected to isoelectric focusing on a Multiphor II electrophoresis chamber (Amersham Pharmacia Biotech) for 90 kVh.

After the first-dimension isoelectric focusing was completed, the focused IPG strip was equilibrated with equilibration buffer (0.2 mM tributylphosphine, 6 M urea, 2% SDS, 375 mM Tris-HCl, pH 8.8, 20% glycerol and 2.5% acrylamide) for 15 min with agitation.

The equilibrated IPG strip was slightly moistened with 1× SDS-PAGE running buffer (192 mM glycine, 0.1% SDS, 24.8 mM Trisma Base), and was then subjected to second-dimension electrophoresis, as follows.

The equilibrated IPG strip was placed onto the top of an 8-16% gradient polyacrylamide gel, and was run at 15 mA per gel for 16 hrs to separate proteins.

(3) Detection of Protein Spots Displaying Increased Expression Levels

The two-dimension gel was washed with 250 ml of triple-distilled water, and was incubated in a fixing solution (40% methanol, 5% phosphoric acid) for 1 hr. The gel was stained with Coomassie brilliant G-250 (Sigma) for 5 hrs and then destained in a destaining solution (1% acetic acid) for 12 hrs to remove excessive staining.

The two-dimension gels, prepared using protein samples obtained from cells cultured in the presence of L-lysine of 0, 250 and 500 mM, were compared with each other using PDQuest software (Bio-Rad). The results are given in FIG. 1. Five protein spots displaying increased expression were detected.

Example 2

Identification of Proteins Whose Expression is Induced by L-Lysine (1) Peptide Extraction from Protein Spots The interested protein spots shown in FIG. 1 were excised from the gels, and were transferred into microtubes. The gel pieces were destained three times with 120 µl of 50% acetonitrile in 25 mM ammonium bicarbonate (pH 7.8,) for 15 min with gentle agitation, and were completely dried. The dried gel pieces were incubated in a trypsin digestion solution (25 mM ammonium bicarbonate, pH 7.8, 0.015 µg/µl trypsin) at 37° C. for 16 hrs to digest proteins in gels. After the in-gel trypsin digestion was completed, the digested gel pieces were covered with 8 µl of a peptide extraction solution (a mixture of 50% acetonitrile and 0.5% trifluoroacetic acid) and was sonicated for 10 min to extract peptides from gels. Then, the gel pieces were centrifuged, and supernatants containing peptides released from gels were recovered and concentrated to a volume of about 5 µl using a freeze dryer.

(2) Protein Identification by Mass Spectrometry

1 µl of each of the concentrated sample was mixed with 1 µl of a matrix solution (10 mg/ml α-cyano-4-hydroxy cinnamic acid, 0.5% trifluoroacetic acid, 50% acetonitrile), was loaded onto a sampling plate for Matrix Assisted Laser Desorption Ionization-Time Of Flight (MALDI-TOF) mass spectrometry, and was dried to be crystallized. Masses of the crystallized peptides were analyzed using a MALDI-TOF mass spectrometer. For protein identification, the measured peptide masses were searched against protein databases of National Center for Biotechnology Information (NCBI) and other sources using MS-Fit software or Profound software. The results are given in Table 1, below. As shown in Table 1, the five protein spots were identified to be encoded by Cgl1910 for spot a, Cgl2134 for spot b, Cgl2754 for spot c, Cgl2818 for spot d, and Cgl3029 for spot e.

TABLE 1

| | Proteins displaying increased expression levels in the presence of lysine | |
|---|---|---|
| Spot | Protein name | Cgl No. |
| a | Transcriptional regulator | 1910 |
| b | Dehydrogenases with different specificities | 2134 |
| c | NADPH-dependent glutamate synthase beta chain and related oxidoreductases | 2754 |
| d | NADPH-dependent glutamate synthase beta chain and related oxidoreductases | 2818 |
| e | Anthranilate synthase component I | 3029 |

Example 3

Construction of Recombinant Vectors Containing Promoter Sequences (1) Amplification of DNA Fragments Corresponding to Putative Promoter Regions The nucleotide sequences of genomic genes of *Corynebacterium glutamicum* have been already fully determined and are well known. Genetic information (Cgl1910, Cgl2134, Cgl2754, Cgl2818 and Cgl3029) of proteins listed in Table 1 was obtained from the NIH GenBank database. In order to amplify putative promoter regions (SEQ ID No. 1: promoter region of Cgl1910, SEQ ID No. 2: promoter region of Cgl2134, SEQ ID No. 3: promoter region of Cgl2754, SEQ ID No. 4: promoter region of Cgl2818, and SEQ ID No. 5: promoter region of Cgl3029) located upstream of each protein ORF, as shown in Table-2, below, primers were designed to contain a BamHI site based on the reported nucleotide sequences, and were synthesized. To amplify the five promoter regions, PCR was carried out using chromosomal DNA of *Corynebacterium glutamicum* ATCC 13032 as a template with the synthesized primers [Sambrook et al., Molecular Cloning, a Laboratory Manual (1989), Cold Spring Harbor Laboratories]. PCR conditions included 25 cycles of denaturation at 94° C. for 1 min, annealing at 58° C. for 1 min and polymerization at 68° C. for 30 sec.

TABLE 2

| Promoter | | Primer sequences | |
|---|---|---|---|
| Cgl1910 | Primer 1 | (SEQ ID No. 6): | TTGGATCC AACCCCGTAGCAACCAGC |
| | Primer 2 | (SEQ ID No. 7): | GAGGATCC GCGCCCAAGTGTACAAATT |
| Cgl2134 | Primer 3 | (SEQ ID No. 8): | ATGGATCC TTGCCTCTAGTGGGACTG |
| | Primer 4 | (SEQ ID No. 9): | TAGGATCC TGAAATCATGCCTTTCTCG |
| Cgl2754 | Primer 5 | (SEQ ID No. 10): | TAGGATCC ATTTCAGCCTGAACCTTC |
| | Primer 6 | (SEQ ID No. 11): | CAGGATCC ATAAAGTTCGATTCCTTAAA |
| Cgl2818 | Primer 7 | (SEQ ID No. 12): | ACGGATCC TGCTTAATTTCCTCGGCA |
| | Primer 8 | (SEQ ID No. 13): | ATGGATCC GTGTTTGAAGTTGCCTTT |
| Cgl3029 | Primer 9 | (SEQ ID No. 14): | AAGGATCC ATGGCTGCGCATACTGTTG |
| | Primer 10 | (SEQ ID No. 15): | ATGGATCC GGGGCACCTACCGAGGAA |

(2) Construction of Vectors for Monitoring Promoter Activity

Figure 2:
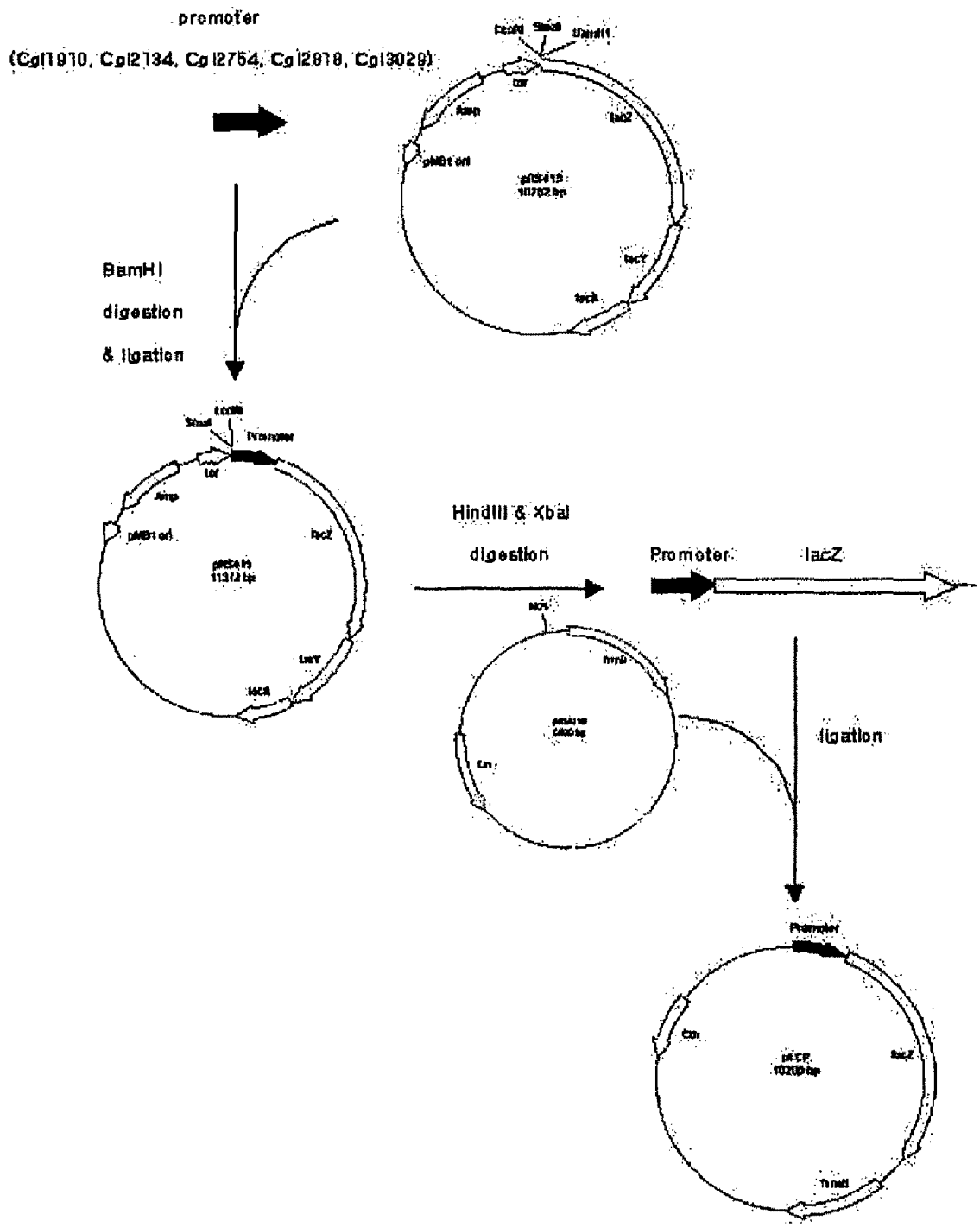
FIG. 2 is a schematic presentation of a process of constructing vectors for monitoring promoter activity, wherein beta-galactosidase was used for detecting promoter activity.

FIG. 2 schematically shows a process of constructing recombinant vectors for monitoring the activity of each putative promoter.

The DNA fragments amplified in the (1) of Example 3 were individually cloned into a BamHI site of pRS415 containing a lacZ gene (Simons, R. W., et al., Gene, 53, 85-96 (1987)). Each recombinant vector was digested with HindIII and XbaI to be cleaved both in front of the inserted putative promoter and in the rear of the lacZ gene, and was electrophoresed on an agarose gel. Each DNA fragment was excised from the gel and purified using a Gel Extraction Kit (Qiagen).

The purified DNA fragments were inserted into a pXMJ19 vector (Jakoby, M. J., et al., Biotechniques, 13, 437-441 (1999)), thus generating vectors for monitoring promoter activity, pLCP-1910, pLCP-2134, pLCP-2754, pLCP-2818 and pLCP-3029. These vectors allow detection of the activity of the putative promoters through measurement of the activity of the lacZ gene product, beta-galactosidase.

The recombinant vectors thus obtained were introduced into competent cells of *Corynebacterium glutamicum* ATCC 13032 according to a method described by van der Rest et al. (Appl. Microbiol. Biotechnol. 52, 541-545, (1999)). The transformed cells were smeared onto LB agar plates (0.5% yeast extract, 1% NaCl, 1% trypton, 1.5% agar) supplemented with 17 mg/ml of chloramphenicol, and were cultured at 30° C. to select grown colonies.

Example 4

Measurement of Activity of Promoter Sequences in *C. glutamicum*

(1) Measurement of Activity of Promoter Sequences in Either the Absence or Presence of 250 mM Lysine The transformed clones were cultured to analyze the activity of promoter sequences, as follows.

Each transformed clone of *Corynebacterium glutamicum* was inoculated at a ratio of 1:20 in a 250-ml baffle flask containing 25 ml of minimal medium (5 g glucose, 5 g ammonium sulfate, 2 g urea, 0.5 g NaCl, 1 g $KH_2PO_4$, 0.5 g $MgSO_4 \cdot 7H_2O$, 200 µg biotin, 100 µg thiamin hydrochloride, 1 ml Trace element solution, in 1 liter distilled water, pH 7.2) either supplemented with 250 mM L-lysine or not, and was incubated at 30° C. with continuous shaking at 200 rpm. When the culture reached the mid-exponential growth phase (an absorbance of 5), the cultured cells were collected by centrifugation, were suspended in 100 mM potassium phosphate buffer (pH 7.0), were lysed by sonication, and then were high speed-centrifuged. 2 µl of the supernatant was used to measure the activity of beta-galactosidase according to Rosenthal's method (Rosenthal, N., Methods Enzymol. 152, 704-720 (1987)). As a result, when cultured in the presence of lysine, the transformed cells displayed beta-galactosidase activity 2.1-fold higher for Cgl1910, 2.1-fold higher for Cgl2134, 2.0-fold higher for Cgl2754, 3.4-fold higher for Cgl2818, and 2.7-fold higher for Cgl3029, than the culturing in the absence of lysine (Table 3). These results indicate that each promoter induces the expression of beta-galactosidase in the presence of lysine.

TABLE 3

Comparison of promoter activity between the absence and presence of lysine

| Promoters | Lysine (mM) | Beta-galactosidase activity (mmol/min/mg) |
|---|---|---|
| Cgl1910 | 0 | 0.28 |
| | 250 | 0.58 |
| Cgl2134 | 0 | 3.30 |
| | 250 | 6.99 |
| Cgl2754 | 0 | 3.09 |
| | 250 | 6.09 |
| Cgl2818 | 0 | 2.75 |
| | 250 | 9.23 |
| Cgl3029 | 0 | 0.50 |
| | 250 | 1.43 |

(2) Measurement of Activity of Promoter Sequences in Either the Absence or Presence of 250 mM NaCl The activity of each promoter was measured according to the same method as in the (1) of Example 4, except that cells were cultured in either the absence or presence of NaCl instead of lysine. The results are given in Table 4, below. As shown in Table 4, similar activity of beta-galactosidase was observed in the two culture conditions, namely the absence and presence of NaCl. These results excluded the possibility of lacZ gene expression to be induced by factors other than lysine, and thus demonstrate that each promoter induces gene expression in specific response to lysine.

TABLE 4

Comparison of promoter activity between the absence and presence of NaCl

| Promoters | NaCl (mM) | Beta-galactosidase activity (mmol/min/mg) |
|---|---|---|
| Cgl1910 | 0 | 0.30 |
|  | 250 | 0.31 |
| Cgl2134 | 0 | 2.59 |
|  | 250 | 2.77 |
| Cgl2754 | 0 | 2.49 |
|  | 250 | 2.05 |
| Cgl2818 | 0 | 1.69 |
|  | 250 | 2.30 |
| Cgl3029 | 0 | 0.87 |
|  | 250 | 0.99 |

INDUSTRIAL APPLICABILITY

As described hereinbefore, the present invention provides promoter nucleic acid molecules that induce gene expression in specific response to lysine, and is thus useful for developing high-titer bacterial strains expressing high levels of a gene encoding a protein of interest.

---

The invention claimed is:

1. A method of inducing expression of a target gene operably linked to a L-lysine-inducible promoter, comprising: i) transforming a host cell with a vector comprising the target gene operably linked to the L-lysine-inducible promoter, wherein the L-lysine-inducible promoter consists of the nucleotide sequence of SEQ ID NO: 4; and ii) culturing the transformed host cell in a medium supplemented with L-Lysine under conditions, wherein said target gene is expressed.

2. The method according to claim 1, wherein the host cell is a coryneform bacterium.

* * * * *